United States Patent
Buse et al.

(10) Patent No.: US 8,178,312 B2
(45) Date of Patent: May 15, 2012

(54) METHOD OF ESTIMATION OF BLOOD GLUCOSE EXCURSIONS IN DIABETIC PATIENTS USING 1,5-ANHYDROGLUCITOL (1,5-AG) ASSAY

(75) Inventors: John B. Buse, Chapel Hill, NC (US); Kathleen Dungan, Columbus, OH (US); Steven D. Wittlin, Rochester, NY (US); Eric A. Button, Kannapolis, NC (US); Shuhei Kato, Tokyo (JP); Toshio Tanabe, Tokyo (JP)

(73) Assignees: Nippon Kayaku Kabushiki Kaisha, Tokyo (JP); Toyota Tsusho America, Inc., New York, NY (US)

( * ) Notice: Subject to any disclaimer, the term of this patent is extended or adjusted under 35 U.S.C. 154(b) by 0 days.

(21) Appl. No.: 11/912,171

(22) PCT Filed: Apr. 21, 2006

(86) PCT No.: PCT/US2006/015091
§ 371 (c)(1),
(2), (4) Date: Dec. 6, 2007

(87) PCT Pub. No.: WO2006/116083
PCT Pub. Date: Nov. 2, 2006

(65) Prior Publication Data
US 2008/0187943 A1 Aug. 7, 2008

Related U.S. Application Data

(60) Provisional application No. 60/674,386, filed on Apr. 22, 2005.

(51) Int. Cl.
*C12Q 1/54* (2006.01)
(52) U.S. Cl. .......................................................... 435/14
(58) Field of Classification Search .................... 435/14
See application file for complete search history.

(56) References Cited

U.S. PATENT DOCUMENTS

| | | | |
|---|---|---|---|
| 5,486,458 | A | 1/1996 | Kojima et al. |
| 5,871,949 | A | 2/1999 | Ebinuma et al. |
| 6,268,166 | B1 | 7/2001 | Kojima et al. |
| 2002/0068310 | A1 | 6/2002 | Sasaki et al. |

FOREIGN PATENT DOCUMENTS

| | | |
|---|---|---|
| JP | 2001-264336 A | 9/2001 |
| WO | WO 03/074071 A1 | 9/2003 |

OTHER PUBLICATIONS

Yamanouchi T. et al., "Clinical usefulness of Serum 1,5-Anhydroglucitol in Monitoring Glycaemic Control", The Lancet, Jun. 1, 1996, vol. 347, No. 9014, pp. 1514-1518.
Yamanouchi T. et al., "Plasma 1,5-Anhydro-D-glucitol as New Clinical Marker of Glycemic Control in NIDDM Patients", Diabetes, vol. 38, pp. 723-729, Jun. 1989.
Kishimoto et al., "1,5-Anhydro-D-glucitol Evaluates Daily Glycemic Excursions in Well-Controlled NIDDM", Diabetes Care, vol. 18, No. 8, Aug. 1995, pp. 1156-1159, XP009097963.
Ceriello et al., "Postprandial Glucose Regulation and Diabetic Complications", Arch Intern Med/vol. 164, Oct. 25, 2004, XP009067639.
Dworacka et al., "1,5-Anhydro-D-glucitol: a novel marker of glucose excursions", UCP Supplement 129, Jul. 2002, pp. 40-44, XP009097980.
K. Borch-Johnsen, The new classification of diabetes mellitus and IGT: a critical approach, Exp. Clin. Endocrinol. & Diabetes, 2001, pp. S86-S93, vol. 109, Suppl 2.
H. Winiarska et al., The usefulness of 1,5-anhydro-D-glucitol determinations in patients with type 2 diabetes mellitus, Diabetologia Polska, 1999, pp. 157-164, vol. 6, No. 3.
M. Dworacka et al., Plasma anhydro-D-glucitol (1,5-AG) as an indicator of hyperglycaemic excursions in pregnant women with diabetes, Diabetic Medicine, Accepted Apr. 6, 2005, pp. 171-175, vol. 23, Diabetes UK.
Kishimoto et al., 1,5-Anhydro-D-glucitol Evaluates Daily Glycemic Excursions in Well-Controlled NIDDM, Diabetes Care, Aug. 1995, pp. 1156-1159, vol. 18, No. 8.
Morimoto, Significance of 1,5 AG for diabetes control indicator, specially relation with hyperglycemia after diet, Medical and Pharmaceutical Sciences, Nov. 25, 2001, pp. 789-793, vol. 46, No. 5 (No English translation.).
Japanese Office Action mailed May 24, 2011, for the corresponding Japanese patent application No. 2008-507917.

*Primary Examiner* — Ralph Gitomer
(74) *Attorney, Agent, or Firm* — Leason Ellis LLP.

(57) ABSTRACT

The invention is a method of measuring blood glucose excursions in general, and postprandial hyperglycemia in diabetic patients in particular, by the 1,5-anhydroglucitol assay (1,5-AG) or A1C/1,5-AG assay combination. 1,5-AG levels and percent changes of 1,5-AG levels in short period are indicative of differing postmeal glucose levels in moderately-controlled diabetic patients with similar A1C levels. Thereby 1,5-AG assay is useful to identify diabetic patients who may be at risk for cardiovascular complications which would not be identifiable by A1C levels alone. Furthermore, ratios of A1C divided by 1,5-AG in each patient are superior indicators to 1,5-AG levels.

6 Claims, 3 Drawing Sheets

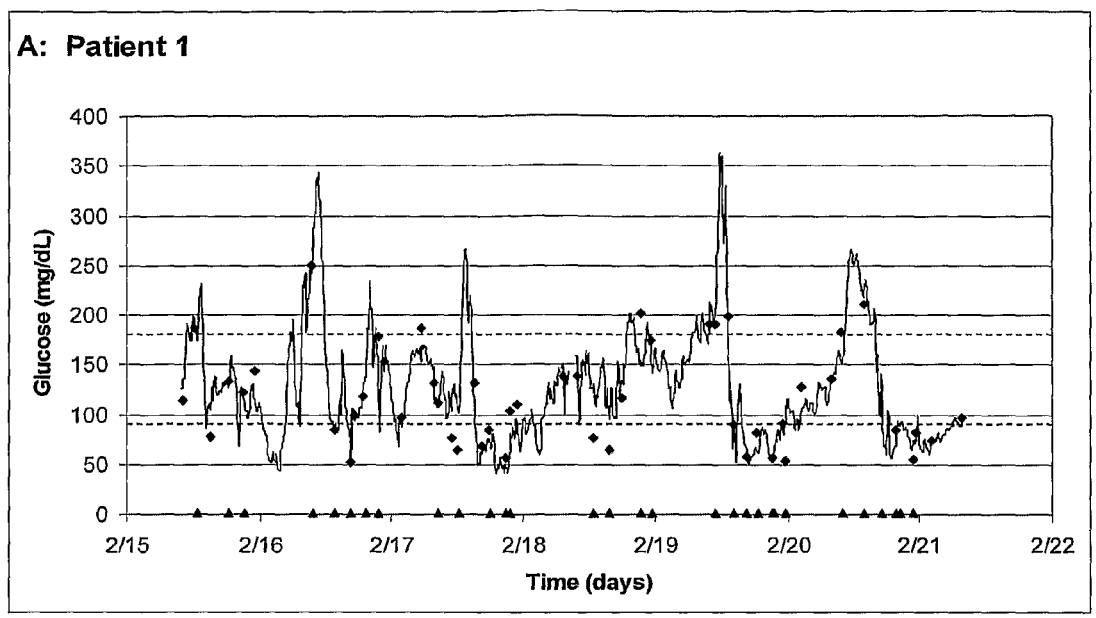
Fig. 1A: Profile of Blood Glucose Excursion in Patient 1.
(52 year old female with type 1 diabetes, A1C 7.43%, 1,5-AG 12.37 µg/mL, AUC-180 8 mg/dL*Day, MPMG 195 mg/dL. Diamonds = paired meter glucose readings. Triangles = meal markers. Dashed lines indicate American Diabetes Association recommended range of 90-180 mg/dL.)

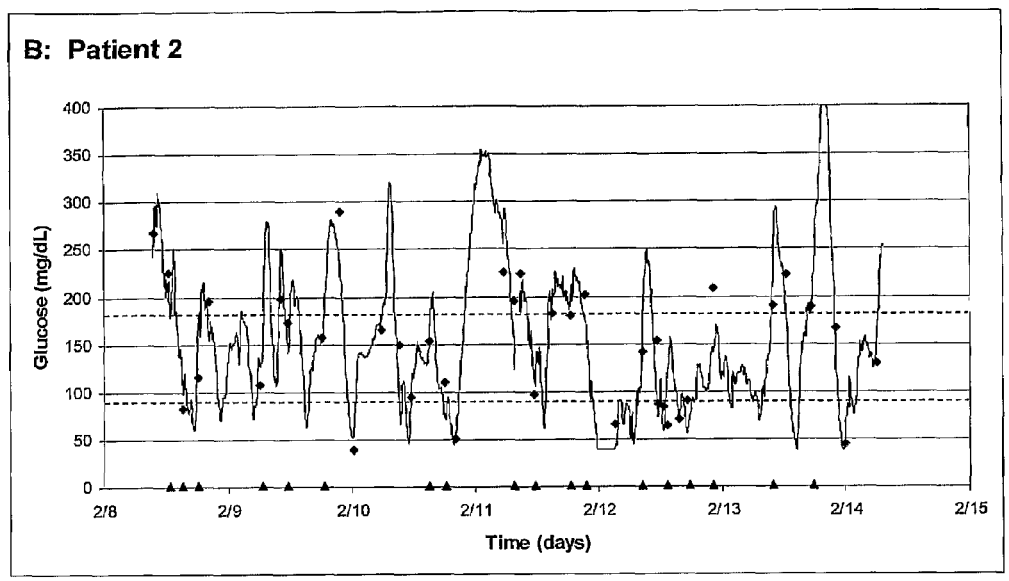
Fig. 1B: Profile of Blood Glucose Excursion in Patient 2.
(49 year old male with type 2 diabetes, A1C 7.27%, 1,5-AG 4.5 µg/mL, AUC-180 22 mg/dL*Day, MPMG 235 mg/dL. Diamonds = paired meter glucose readings. Triangles = meal markers. Dashed lines indicate American Diabetes Association recommended range of 90-180 mg/dL.)

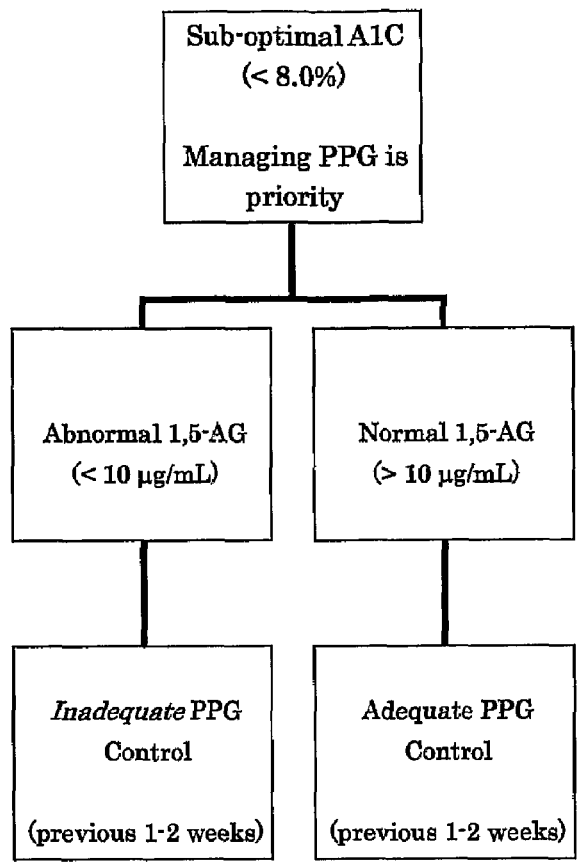
Fig. 2: Postprandial Glucose Control Diagnostic Algorithm with 1,5-AG as Adjunct to A1C to Reflect Postprandial Hyperglycemia

METHOD OF ESTIMATION OF BLOOD GLUCOSE EXCURSIONS IN DIABETIC PATIENTS USING 1,5-ANHYDROGLUCITOL (1,5-AG) ASSAY

CROSS-REFERENCE TO PRIOR APPLICATION

This is a U.S. National Phase Application under 35 U.S.C. §371 of International Patent Application No. PCT/US2006/015091 filed Apr. 21, 2006, which claims the benefit of U.S. Provisional Application No. 60/674,386, filed Apr. 22, 2005, both of which are incorporated by reference herein. The International Application was published in English on Nov. 2, 2006 as WO 2006/116083 A1 under PCT Article 21(2).

FIELD OF THE INVENTION

The invention is a method of measuring blood glucose excursions, including postprandial hyperglycemia in diabetic patients, by the 1,5-anhydroglucitol assay (1,5-AG) or A1C/1,5-AG assay combination. 1,5-AG levels and percent changes of 1,5-AG levels in short period are indicative of differing postmeal glucose levels in moderately-controlled diabetic patients with similar A1C levels. Thereby 1,5-AG assay is useful to identify diabetic patients who may be at risk for cardiovascular complications which would not be identifiable by A1C levels alone. Furthermore, ratios of A1C divided by 1,5-AG in each patient are superior indicators to 1,5-AG levels.

INCORPORATION BY REFERENCE

The following references are referred to by their numbers in parenthesis in this specification and incorporated herein by reference.
1. M. Tominaga et al., Impaired glucose tolerance is a risk factor for cardiovascular disease, but not impaired fasting glucose. Diabetes Care, 22, (6), 920-924 (1999)
2. Q. Qiao et al., Comparison of the fasting and the 2-h glucose criteria for diabetes in different Asian cohorts. Diabetologia, 43, (12), 1470-1475 (2000)
3. DECODE Study Group, Glucose tolerance and cardiovascular mortality: comparison of fasting and 2-hour diagnostic criteria. Arch. Intern. Med, 161 (3), 397-405 (2001)
4. Y. Akanuma et al., Urinary excretion of 1,5-anhydro-D-glucitol accompanying glucose excretion in diabetic patients. Diabetologia, 31, 831-835 (1988)
5. T. Yamanouchi et al., Plasma 1,5-Anhydro-D-Glucitol as New Clinical Marker of Glycemic Control in NIDDN Patients. Diabetes, 38, 723-729 (1989)

BACKGROUND OF THE INVENTION

The importance of tight glycemic control to prevent complications has been well documented. More recently, studies indicate that postprandial glucose is an independent risk factor for the development of macrovascular complications (1-3). Many well controlled patients with diabetes have significant postprandial hyperglycemia. Therefore, an alternative marker that more robustly reflects postprandial glucose excursions than A1C measurements could be beneficial in the long-term care of patients with diabetes. Here, "glucose excursion" means a movement in the amount of glucose in blood from one level to another, usually with the implication that the amount will eventually return to the original level, and "A1C" or equivalently "HbA1c" refers to glycosylated hemoglobin.

1,5-Anhydro-D-glucitol (hereafter abbreviated to 1,5-anhydroglucitol or "1,5-AG") is a naturally occurring dietary polyol having a very similar chemical structure to glucose and present in human cerebrospinal fluid and plasma. Its quantity in plasma is stable in healthy subjects and is reduced in those with certain diseases, particularly with diabetes.

Plasma levels of 1,5-AG fall as urinary glucose appears, generally at around 180 mg/dL, which is the renal threshold for glucose and the upper limit of normal postprandial glucose. Thus, the 1,5-AG test responds sensitively and rapidly to serum glucose levels, reflecting even transiently ascending serum glucose above the renal threshold for glucosuria within a few days (4,5). In contrast, A1C is a reflection of average glucoses over a much longer period of time (2-3 months), encompassing both hyperglycemic and hypoglycemic periods. Therefore, glycemic excursions are "averaged out" in the setting of A1C monitoring.

In clinical setting, 1,5-AG in plasma or serum can be measured conveniently by a commercial kit based on colorimetric enzymatic method using an enzyme that oxidizes 1,5-AG.

SUMMARY OF THE INVENTION

Our results have significant clinical implications. In a subset of moderately controlled patients (A1C 6.5 to 8.0%), there may be significant postprandial hyperglycemia present. Furthermore, at similar A1C levels, there may be differing postprandial glucose levels which are reflected by 1,5-AG levels. Therefore, 1,5-AG levels are indicative of differing postmeal glucose levels in moderately controlled patients with similar A1C levels—thereby identifying diabetic patients who may be at risk of cardiovascular complications.

In the clinical setting, A1C and 1,5-AG may then be used sequentially, with the A1C assay first being used to identify patients who are moderately controlled (A1C 6.5 to 8.0%), and then using the 1,5-AG assay to determine differing postmeal glucose levels.

The present invention relates to a method to evaluate blood glucose excursions in general, and postprandial hyperglycemia in diabetic patients in particular, that is characterized by 1,5-anhydroglucitol value in blood.

The invention further relates to a method to evaluate blood glucose excursions in general, and postprandial hyperglycemia in diabetic patients in particular, using a calculation formula or a table that estimates a mean maximum postprandial glucose level based on 1,5-anhydroglucitol value.

The invention further relates to a method to evaluate blood glucose excursions in general, and postprandial hyperglycemia in diabetic patients in particular, that is characterized by a combination of 1,5-anhydroglucitol value and other glycemic control marker value, wherein the other glycemic control marker may be A1C or fasting plasma glucose.

The invention further relates to a method to evaluate blood glucose excursions in general, and postprandial hyperglycemia in diabetic patients in particular, using a ratio of A1C value to 1,5-anhydroglucitol value or a product of A1C value and 1,5-anhydroglucitol value as an index.

The invention further relates to a method to evaluate blood glucose excursions in general, and postprandial hyperglycemia in diabetic patients in particular, using a change or a percent change of 1,5-anhydroglucitol values obtained from at least 2 serial measurements over a short time period as an index, wherein the short time period may be 2 to 7 days.

Furthermore, in the present invention, the diabetic patients may be moderately controlled patients or patients whose A1C levels are 6.5 to 8.0%.

The invention further relates to a method to estimate a risk of cardiovascular complications of a diabetic patient based on a measurement of his or her 1,5-anhydroglucitol value.

The invention further relates to a device to evaluate blood glucose excursions in general, and postprandial hyperglycemia in diabetic patients in particular, which contains a unit to measure 1,5-anhydroglucitol values in blood.

DESCRIPTION OF THE FIGURES

FIGS. 1A and 1B show profiles of blood glucose excursions obtained from 2 patients who have similar A1C values but different 1,5-AG values.

FIG. 2 shows a diagnostic algorithm to control postprandial glucose using a measured 1,5-AG value.

DESCRIPTION OF THE INVENTION

The fact that 1,5-AG levels reflect glucosuria suggests that the 1,5-AG test may be an effective measure of blood glucose excursions in general, and elevated postprandial glucose excursions in diabetic patients in particular, commonly referred to as postprandial hyperglycemia. The 1,5-AG assay may be a complementary indicator of glycemic control to A1C with specific relevance to assessing postprandial hyperglycemia.

With the advent of the Continuous Glucose Monitoring System ("CGMS") which provides minute-by-minute recording of glucose levels, it is now possible to compare CGMS profiles to serum levels of 1,5AG—providing a direct demonstration between 1,5-AG and the occurrence of postprandial hyperglycemia. This study examined the role of 1,5-AG as a more timely assessment of diabetic patients who are seemingly in good control, as reflected by A1C, but may be deteriorating as a result of transient glycemic excursions postprandially.

In order to determine the relationships between the 1,5-AG assay and other glycemic tests (A1C, fructosamine, and fasting plasma glucose) and postprandial hyperglycemia, continuous glucose measurements as performed by CGMS were compared to glycemic test values in moderately controlled patients as defined by A1C levels.

Patients (n=34) age 18 to 75 with type 1 or type 2 diabetes and an A1C between 6.5 and 8.0% (moderately controlled patients) with stable glycemic control were tested. A CGMS monitor was worn for two consecutive 72-hour periods and patients checked their 7-point fingerstick glucose profiles.

Area under the curve for glucose above 180 mg/dL ("AUC-180") and mean glucose as determined by CGMS over each 72-hour period were compared to 1,5-AG (µg/mL), fructosamine (µmol/l) and A1C (% Hb) at baseline, on day 4 and day 7.

Correlation coefficients and multivariate analysis of above relationships were explored.

The results indicated that 1,5-AG had significantly better correlation with postprandial glucose excursions than A1C or fructosamine, and that 1,5-AG showed significant differences between the two groups with high and low degrees of postprandial glucose excursions. A1C, fructosamine, and fasting plasma glucose did not show differences between these groups. Furthermore, CGMS profiles showed that postmeal glucose levels did not reach their respective maxima at the same time after meals. Thus a postprandial glucose level measured by a conventional method such as a self-monitoring glucose meter does not reflect the entire status of postprandial glucose excursions. 1,5-AG is the only known marker which can conveniently determine the exact status of postprandial glucose excursions.

Additionally, blood sugar control status is very different in each diabetic patient. Some patients may have high fasting plasma glucose levels and high glucose excursions. Other patients may have near-normal fasting plasma glucose levels but high glucose excursions. Well-controlled patients have normal or near-normal fasting plasma glucose levels and similar levels of glucose excursions as in healthy subjects.

At the present time, many types of drugs are used for the treatment of diabetic patients. Each type of drugs has different mechanism of actions. α-glucosidase inhibitor, for example, reduces postprandial hyperglycemia as a fast-acting insulin secretion agent or short-acting insulin. Sulfonylurea antidiabetic agents are used to treat patients with high fasting plasma glucose levels. Patients with near-normal fasting plasma glucose and high glycemic excursions may be treated with drugs that reduce postprandial hyperglycemia. It is very important to choose the most suitable drug for each patient. 1,5-AG is a useful indicator in choosing the most suitable drug for the treatment of diabetic patients.

1,5-AG provides information on blood glucose excursions in general, and postprandial hyperglycemia in diabetic patients in particular. Mean maximum plasma glucose level during the past several days can also be estimated from the measured 1,5-AG value.

1,5-AG values are correlated only moderately to A1C, fructosamine or glycated albumin values, although those glycemic control makers reflect average plasma glucose levels of diabetic patients. If 1,5-AG value is lower than the 1,5-AG value estimated from other glycemic control maker, especially A1C, we can make a judgment that the patient has high glucose excursions. It is also useful to use a ratio of A1C value to 1,5-AG value or a product of A1C value and 1,5-AG value as an index for judgment of high glucose excursions.

A combination of fasting plasma glucose and 1,5-AG is also useful. In a case that a 1,5-AG value is low while a fasting plasma glucose value is almost in the normal range, it appears that a patient has severe postprandial hyperglycemia.

When the degree of glucose excursions changes during a short period, 1,5-AG value also changes accordingly in that period. 1,5-AG can thus be used for confirming the effect of drugs during initial therapy. The confirmation with 1,5-AG can be done within 7 days. Percent changes of 1,5-AG values also can be used for this confirmation.

1,5-AG value may vary significantly among moderately controlled diabetic patients with A1C value of up to 8.0% in which postprandial glucose elevations predominate. The usefulness of 1,5-AG to evaluate blood glucose excursions, including postprandial glucose excursions, is particularly pronounced in the A1C range from 6.5 to 8.0%. A1C can be used to select patients who need to be measured with 1,5-AG.

Study Methodology

Patient population: N=34 diabetic patients evenly distributed between patients with type 1 and type 2 diabetes.

Inclusion Criteria:

Age 18-75, male and female

Diagnosed with diabetes type 1 or type 2

A1C 6.5-8.0% as measured by Bayer DCA-2000 point of care meter

Stable glycemic control as defined by no recently noted deterioration or improvement in control (patient-reported) and at least 1 prior A1C measurement in the prior 6 months with no change across measures of greater than 0.5%

Monitoring glucose at least twice daily (type 2) or three or more times daily (type 1) by patient report Exclusion criteria:

Pregnancy or lactation

Medical history of cancer, end-stage liver disease, chronic renal failure (Creatinine>2.0 mg/dL), malnutrition (unintended weight loss >10% in one year), connective tissue disease Significant anemia (hemoglobin <10 g/dL), known hemoglobinopathy, recent blood donation, hemolysis, recent surgery with blood loss.

Unstable retinopathy or recent (<6 month) retinal procedure.

Patients currently taking investigational drugs or active participants of any treatment trial.

Non-English speaking subjects

Unwilling or unable to self-monitor blood glucose

Hypoglycemia requiring assistance in the prior 3 months.

Sequence of Events:

Day 1: Blood for 1,5-AG, A1C, fructosamine and fasting plasma glucose ("FPG") was drawn. The CGMS device was inserted and the patient was taught how to manage the device.

Day 4: Blood tests were repeated and the CGMS sensor was replaced at a new site. A 24-hour urine was collected on day 3 and turned in on day 4. Glucose logs were collected and meters were downloaded.

Day 7: Blood test was repeated. The CGMS device was removed and the site was inspected. Glucose logs were collected and meters were downloaded.

CGMS device: Patients wore a subcutaneously inserted CGMS (MiniMed) device that was inserted on day 1 and removed on day 7. The site was changed on day 4. The device was used as per FDA approved labeling. A trained healthcare professional introduced a tiny sensor using local antiseptic into the skin of the abdomen, an automatic insertion device and an introducer needle that was removed immediately. The sensor sits just beneath the skin and is secured with tape to keep it in place. The sensor was connected to a monitor, which records readings that were only accessible after downloading to a laptop computer at the healthcare provider's office.

Fingerstick glucose: Patients were asked to check fingerstick glucoses and keep a log of morning fasting, pre-meal, 2-hour postprandial, and bedtime glucoses (~7 times) daily throughout days 1 through 6 of the study.

Glycemic assay: 1,5-AG was measured with GlycoMark, a brand name for 1,5-AG test, purchased from Tomen America Inc., NY. A1C and fructosamine were measured by the conventional methods. Three blood samples drawn at day1, day4 and day7 for each patient were measured.

Postprandial Variables and Analysis

Postprandial Variables Tested:

To determine the relationship of glycemic tests to glucose excursions and postprandial hyperglycemia, several variables measured by CGMS were used, including:

1) AUC-180 (3 days and 7 days)—a measure of the total area of glucose excursions above 180 mg/dL was determined for each patient for each 72-hour time period (3 days) and then combined for the entire CGMS testing period (7 days). AUC-180 is the primary variable used to reflect glucose excursions.

2) Average Postmeal (Maximum) Glucose (mg/dL)—the maximum height of each postmeal glucose excursion was determined and then averaged for each patient for three meals (breakfast, lunch, and dinner). It should be noted that not all patients inputted meal markers into the CGMS units. Therefore, average postmeal maximums were determined only in a subset of patients. Elevated average postmeal glucose levels are specifically indicative of postprandial hyperglycemia.

3) Postprandial Index—a comprehensive glucose excursion and postprandial hyperglycemic index ("postprandial index (PI)") was formulated by incorporating four variables—maximum glucose levels for post-breakfast, post-lunch, post-dinner, and AUC-180 (7 days). In other words, PI was calculated with the above four independent variables through multiple regression. That is, coefficients and an intercept were determined by multiple linear regression analysis with each average glycemic assay value, a ratio of those, or a percent change of 1,5-AG.

Correlation/Multivariate Analyses

The averages of the three values of the glycemic tests (1,5-AQ, A1C, and fructosamine) for each patient over the 3-day and 7-day period were compared to the postprandial variables outlined above. Correlation (Pearson) and multivariate analyses were then performed.

EXAMPLE 1

Glycemic Assays vs. Postprandial Variables (Correlation and Multivariate Analyses)

Average AUC-180 (7 days and 3 days) vs. Glycemic Assay Values

As the study was designed to reflect the overall metabolic state of the patient, average values for the lab tests over the entire 7-day period were utilized and correlated to AUC-180 (7 days). In the case of AUC-180 (3 days), absolute assay values were used at the end of each 3-day period. Correlation (R values) and corresponding p values (p) are presented below. Comparative correlations were computed using Steiger Z values as presented in the table.

|  | A1C (%) | 1,5-AG(μg/mL) | Fructosamine (μmol/l) |
|---|---|---|---|
| AUC-180 7 days (N = 34) (mg/dL*Day)* | R = 0.36 p = 0.02 | R = −0.48 p = 0.002 | R = 0.33 p = 0.03 |
| AUC-180 at End-Interval 1 3-day period (N = 34) (mg/dL*Day)** | R = 0.23 p = 0.09 | R = −0.36 p = 0.02 | R = 0.16 p = 0.18 |
| AUC-180 at End-Interval 2 3-day period (N = 33) (mg/dL*Day)*** | R = 0.35 p = 0.02 | R = −0.42 p = 0.008 | R = 0.37 p = 0.02 |

End-interval for interval 1 is visit #2 (study mid-point) and for interval 2 is visit #3 (study end). Comparative correlations were calculated and Steiger Z(1 bar) values were AUC-180 Overall/A1C vs. AUC-180 Overall/1,5-AG (Z = −3.01, p < .01)*, AUC-180 Interval 1/A1C vs. AUC-180 Interval 1/1,5-AG (Z = −1.99, p < .05), AUC-180 Interval 2/A1C vs. AUC-180 Interval 2/1,5-AG (Z = −2.61, p < .01)*.

The 1,5-AG assay reflects AUC-180 (3 days and 7 days) better than the A1C and fructosamine assays in both time periods. A1C correlates better than fructosamine (vs. AUC). As AUC-180 is a key measure of glucose excursions and postprandial hyperglycemia, these data indicate that 1,5-AG levels reflect excursions and postprandial hyperglycemia to a greater extent than A1C or fructosamine.

Average Maximum Postmeal Glucose vs. Average Glycemic Assay Values

As is the case with several published postprandial assay studies, maximum postmeal glucose levels are measured as a key index of postprandial hyperglycemia. Average postmeal maximum glucose levels for each meal (breakfast, lunch, and dinner) were correlated to average glycemic assay values. The three postmeal glucose maximum values were then used in a multivariate analysis as independent variables to compare to average glycemic assays values.

|  | Avg. A1C (%) | Avg. 1,5-AG (µg/mL) | Avg. Fructosamine (µmol/l) |
| --- | --- | --- | --- |
| Avg. Postmeal Max (Breakfast) N = 20 (mg/dL) | R = 0.12 p = 0.31 | R = −0.38 p = 0.05 | R = −0.003 p = 0.494 |
| Avg. Postmeal Max (Lunch) N = 23 (mg/dL) | R = 0.19 p = 0.19 | R = −0.22 p = 0.15 | R = 0.06 p = 0.39 |
| Avg. Postmeal Max (Dinner) N = 22 (mg/dL) | R = 0.25 p = 0.13 | R = −0.54 p = 0.004 | R = 0.35 p = 0.06 |
| Combined Postmeal Max (Breakfast, Lunch, Dinner) - Multiple Regression N = 19 | R = 0.25 | R = −0.57 | R = 0.36 |

1,5-AG values correlated better with each postmeal glucose maximum variable (breakfast, lunch, and dinner) than either A1C or fructosamine. In addition, the multivariate analysis (3 postmeal maximum variables combined) indicated that 1,5-AG is significantly more predictive of postprandial hyperglycemia than either A1C or fructosamine.

The analyses comparing glycemic test values to postprandial variables (AUC-180 and Postmeal Maximum Glucose Values) indicate that the 1,5-AG assay reflects postprandial hyperglycemia more robustly than established glycemic assays (A1C and fructosamine).

EXAMPLE 2

"Postprandial Index" vs. Average Glycemic Assay Values

The postprandial index ("PI") was then compared to each average glycemic assay value. The postprandial index is a comprehensive glucose excursion and postprandial hyperglycemic function capturing both postmeal and AUC-180 variables as previously described.

|  | Avg. A1C (%) | Avg. 1,5-AG (µg/mL) | Avg. Fructosamine (µmol/l) |
| --- | --- | --- | --- |
| Postprandial Index (PI) N = 19 | R = 0.36 | R = −0.58 | R = 0.36 |

The multivariate analysis indicated that 1,5-AG has a significantly higher absolute R value than A1C or fructosamine—indicating that the 1,5-AG assay reflects glucose excursions and postprandial hyperglycemia more robustly than established glycemic assays (A1C and fructosamine).

EXAMPLE 3

1,5-AG Changes vs. Postprandial Index

In addition to correlating average 1,5-AG assay values to the postprandial index, changes in 1,5-AG values (% change from second patient visit to the third patient visit) were correlated to the postprandial index. The R value was 0.82, equating to R-squared of 0.67. In other words, the change in 1,5-AG levels explained 67% of the variations in the postprandial index. It should be noted that there was no statistically significant relationship between fructosamine changes or A1C changes and the postprandial index.

These data indicate that measuring 1,5-AG values over specific time periods is useful in monitoring glucose excursions and postprandial hyperglycemia. This is particularly useful in monitoring the effect of therapy specifically targeted to postprandial hyperglycemia.

EXAMPLE 4

1,5-AG and A1C Assay Combination vs. Postprandial Index

In order to determine the relationship of a combination of 1,5-AG and A1C assay values to postprandial hyperglycemia, a ratio A1C divided by 1,5-AG ("A1C/1,5-AG") was compared to the postprandial index and correlation/multivariate analyses were conducted. Correlations of 1,5-AG and A1C independently versus the postprandial index are presented for comparative purposes.

|  | Avg. A1C (%) | Avg. 1,5-AG (µg/mL) | Avg. A1C/Avg. 1,5-AG Ratio |
| --- | --- | --- | --- |
| Postprandial Index (PI) N = 19 | R = 0.36 | R = −0.58 | R = 0.66 |

The ratio of A1C/1,5-AG has a stronger correlation to the postprandial index than either the A1C assay or 1,5-AG assay alone—indicating that a combination of the two assays is more predictive of glucose excursions and postprandial hyperglycemia. It is also apparent from the correlation/multivariate analyses that 1,5-AG contributes much more significantly than A1C to the postprandial index. This is also supported by multivariate analyses in which both the A1C and 1,5-AG assay variables are compared to individual postprandial variables—showing that 1,5-AG (when combined with A1C values) is driving much of the relationship with the individual postprandial variables. Overall, the A1C/1,5-AG assay ratio reflects glucose excursions and postprandial hyperglycemia more robustly than each assay independently—although 1,5-AG is the primary variable in driving postprandial index.

EXAMPLE 5

Clinical Utility—1,5-AG Assay as Adjunct to A1C Assay to Reflect Postprandial Hyperglycemia As described in the previous section, the A1C/1,5-AG combined assay ratio reflects glucose excursions and postprandial hyperglycemia more robustly than each assay independently—although 1,5-AG is the primary variable in driving the postprandial index. To investigate the clinical potential of these findings, 34 moderately controlled patients (A1C 6.5 to 8.0%) were sorted by their total AUC-180 values and subdivided into two populations—"Low Total AUC-180 Values" (17 patients) and "High Total AUC-180 Values" (17 patients). The table below presents A1C and 1,5-AG assay parameters as well as postprandial variables.

|  | Total AUC-180 Mean (mg/dL * Day) | MPMG (mg/dL) | A1C Mean (%) | 1,5-AG Mean (μg/mL) | Fructosamine Mean (μmol/l) | Fasting Glucose Mean (mg/dL) |
|---|---|---|---|---|---|---|
| Sorted 17 "Low" Total AUC-180 | 7.18 +/− 4.45 | 180 +/− 28 (N = 12) | 7.20 +/− 0.71 | 8.00 +/− 4.26 | 313 +/− 55 | 146 +/− 42 |
| Sorted 17 "High" Total AUC-180 | 19.76 +/− 3.88 | 230 +/− 36 (N = 11) | 7.38 +/− 0.35 | 5.58 +/− 2.04 | 319 +/− 43 | 158 +/− 33 |
| p-value | <0.0001 | 0.001 | 0.34 | 0.04 | 0.70 | 0.36 |

Although A1C, fructosamine and fasting glucose values are very similar between the two groups, 1,5-AG and the mean maximal glucose value of postmeal glucose excursion after breakfast, lunch, or dinner (MPMG) are significantly different between the two. Moreover, the normal range of 1,5-AG in a U.S. population is above 6.8 μg/mL. This is consistent with what is observed for the "high total AUC-180" group in the above table, in which the range of 1,5-AG values is below 6.0 μg/mL—reflecting significant postprandial hyperglycemia. Thus, specific 1,5-AG ranges can be related to postprandial glucose levels, although A1C levels are very similar.

Additionally, and consistent with the results obtained with the combined A1C/1,5-AG assay ratio, the partial correlation of 1,5-AG with AUC-180 (controlling for A1C) was −0.38 (p=0.01), a sizeable correlation relative to the correlation of 1,5-AG as an independent variable and AUC-180 (r−0.48)—indicating for a given level of A1C, there is a significant relationship between 1,5-AG and AUC-180. These partial correlation analyses provide additional evidence that the 1,5-AG assay is a useful adjunct to the A1C assay to reflect glucose excursions, including postprandial hyperglycemia.

CGMS can determine exact postprandial glucose levels that are only crudely captured by such an index as Total AUC-180 value or MPMG value, but CGMS is also tedious and time consuming. CGMS is not practical for the actual clinical setting to treat many patients. 1,5-AG is the only practical marker reflecting postprandial glucose excursion levels.

EXAMPLE 6

Clinical Utility—1,5-AG Assay and Postmeal Glucose Reference Range Table

By correlating average maximal postmeal glucose levels (averages of all breakfast, lunch and dinner postmeal glucose values, n=23) and mean 1,5-AG assay values, several regression formulas were calculated as presented below.

| Simple Regression X-Variable: 1,5-AG Mean Y-Variable: Mean overall postmeal max | | | | | |
|---|---|---|---|---|---|
| | N | A | B | R | R-Square |
| Y = A + B * X | 23 | 241.876239 | −5.056443788 | 0.50 | 0.25 |
| Y = A * X^B | 23 | 297.1519269 | −0.208491031 | 0.56 | 0.31 |
| Y = A * e^(B * X) | 23 | 239.2020874 | −0.023616958 | 0.49 | 0.24 |
| Y = A + B * ln(X) | 23 | 292.2448929 | −46.71548656 | 0.60 | 0.36 |
| Y = A + B/X | 23 | 156.9116251 | 273.6912986 | 0.68 | 0.46 |

-continued

| Simple Regression X-Variable: 1,5-AG Mean Y-Variable: Mean overall postmeal max | | | | | |
|---|---|---|---|---|---|
| | N | A | B | R | R-Square |
| Y = 1/(A + B * X) | 23 | 0.004223418 | 0.00011387 | 0.47 | 0.22 |
| Y = X/(A + B * X) | 23 | −0.005167608 | 0.005965369 | 0.53 | 0.29 |

The optimal regression approach is a hyperbolic regression with an R value of 0.68 (Y=A+B/X). Using the formula represented by [Mean Postmeal Max=156.91+273.69/Average 1,5-AG], a reference range table matching 1,5-AG levels with the corresponding average maximal postmeal glucose levels was computed and is presented below. This reference range table may be used clinically to derive approximate postmeal glucose levels from measured 1,5-AG values.

| Relationship of 1,5-AG Values to Approximate Average Postmeal Blood Glucose Levels (Moderately-Controlled Patients) | |
|---|---|
| 1,5-AG (μg/mL) | Approximate Mean Postmeal Maximum Blood Glucose (mg/dL) |
| >12 | <180 |
| 10 | 185 |
| 8 | 190 |
| 6 | 200 |
| 4 | 225 |
| <2 | >290 |

EXAMPLE 7

Clinical Utility—Using the 1,5-AG Assay in Clinical Practice

To further substantiate the utility of the 1,5-AG assay to measure glucose excursions and postprandial hyperglycemia in clinical practice, data from 2 representative patients are presented in FIGS. 1A and 1B. Patient 1 of FIG. 1A has a similar A1C (7.43%) to patient 2 of FIG. 1B (7.27%). In contrast, the 1,5-AG for patient 1 is within the normal range at 12.37 μg/mL, as opposed to patient 2 at 4.5 μg/mL. This also corresponds to a lower AUC (8 vs. 22 mg/dL*Day) and a lower MPMG (195 mg/dL vs. 235 mg/dL) in patient 1 vs. patient 2, respectively. The CGMS tracings are also shown for each patient in the Figures and clearly demonstrate much greater glucose excursions in the patient with abnormal 1,5-AQ namely, patient 2.

These representative patients clearly demonstrate that the 1,5-AG assay is reflective of varying postmeal glucose levels, despite similarities in A1Cs. This is particularly important in moderately controlled or suboptimal patients (A1C levels 6.5 to 8.0%) in which postprandial glucose elevations predominate.

In clinical practice, A1C and 1,5-AG may be used sequentially, by first employing the A1C assay to identify patients who are moderately controlled (A1C 6.5 to 8.0%) and then using the 1,5-AG assay to determine the extent of postprandial glucose excursions (see the diagnostic algorithm in FIG. 2 and the reference range table in Example 6 above). If the A1C is above target and the 1,5-AG is normal, therapy targeting basal glucose may be more useful. On the other hand, if the A1C is above target and the 1,5-AG is low, targeting postprandial glucose elevations may be more productive. This may involve more intensive postprandial monitoring or the addition of agents that specifically address postprandial hyperglycemia.

Due to the rapid response of 1,5-AG to changes in glycemia, serial 1,5-AG measurements may be useful in assessing postprandial hyperglycemia. This may be particularly valuable in examining the effect of therapy specifically targeted to postprandial glucose control. In most patients, it may be difficult to discern whether the true barrier to perfect glycemic control lies with inadequate prandial or basal glycemic treatment. There is often insufficient self-monitoring data to make the intricate adjustments that may be necessary in patients with type 1 diabetes on intensive insulin therapy. On the other hand, many patients with type 2 diabetes who are on oral agents check their blood glucoses only once per day or even less frequently, generally in the fasting state. 1,5-AG may be useful as an adjunct to A1C in these settings.

What is claimed is:

1. A method of estimating a mean postmeal maximum blood glucose level in a person, said method comprising the steps of:

measuring a 1,5-anhydroglucitol value in a sample of the the person's blood; and calculating an estimated mean postmeal maximum blood glucose level by means of one of the following function equations;

$$Y = A + B/X,$$

$$Y = A + B*\ln(X),$$

$$Y = A*X^B, \text{ or}$$

$$Y = X/(A + B*X),$$

where A and B are constant numbers; X is the measured 1,5-anhydroglucitol value and Y is the estimated mean postmeal maximum blood glucose level.

2. The method of claim 1, wherein a person is a diabetic patient.

3. The method of claim 2, wherein the diabetic patient has a level of glycosylated hemoglobin, also known as HbA1c, between 6.5 and 8.0% inclusive.

4. The method of claim 1, wherein the estimated mean postmeal maximum blood glucose level is a mean of postmeal maximum blood glucose levels during several days before the sample is taken.

5. The method of claim 1, wherein the mean postmeal maximum blood glucose level is defined as an average of three maximum heights of glucose levels measured after three meals (breakfast, lunch and dinner).

6. The method of claim 1, wherein glucose levels measured by a minute-by-minute recording system known as a Continuous Glucose Monitoring System, or CGMS, are used to obtain function equations.

* * * * *